(12) United States Patent
Leiboff

(10) Patent No.: US 7,021,316 B2
(45) Date of Patent: Apr. 4, 2006

(54) DEVICE AND METHOD FOR TACKING A PROSTHETIC SCREEN

(75) Inventor: Arnold Robert Leiboff, Stony Brook, NY (US)

(73) Assignee: Tools For Surgery, LLC, Stony Brook, NY (US)

( * ) Notice: Subject to any disclaimer, the term of this patent is extended or adjusted under 35 U.S.C. 154(b) by 43 days.

(21) Appl. No.: 10/636,841

(22) Filed: Aug. 7, 2003

(65) Prior Publication Data

US 2005/0049635 A1    Mar. 3, 2005

(51) Int. Cl.
*A41B 1/10*    (2006.01)
(52) U.S. Cl. .................. 128/898; 606/151; 606/222
(58) Field of Classification Search ............ 623/23.72; 606/228, 151, 222; 128/898
See application file for complete search history.

(56) References Cited

U.S. PATENT DOCUMENTS

| 3,123,077 | A | | 3/1964 | Alcamo |
| 3,494,006 | A | * | 2/1970 | Brumlik ................... 24/447 |
| 4,069,825 | A | * | 1/1978 | Akiyama .................. 606/158 |
| 4,133,339 | A | * | 1/1979 | Naslund ................... 132/323 |
| 4,548,202 | A | | 10/1985 | Duncan |
| 4,741,330 | A | * | 5/1988 | Hayhurst ................... 606/144 |
| 5,041,129 | A | * | 8/1991 | Hayhurst et al. ........... 606/232 |
| 5,053,047 | A | | 10/1991 | Yoon |
| 5,123,913 | A | * | 6/1992 | Wilk et al. ................. 606/232 |
| 5,269,809 | A | * | 12/1993 | Hayhurst et al. ........... 606/232 |
| 5,374,268 | A | | 12/1994 | Sander |
| 5,683,417 | A | | 11/1997 | Cooper |
| 6,241,747 | B1 | * | 6/2001 | Ruff ......................... 606/216 |
| 6,270,517 | B1 | * | 8/2001 | Brotz ........................ 606/228 |
| 6,447,524 | B1 | | 9/2002 | Knodel et al. |
| 6,478,809 | B1 | | 11/2002 | Brotz |

* cited by examiner

*Primary Examiner*—Gary Jackson
(74) *Attorney, Agent, or Firm*—Brian Roffe

(57) ABSTRACT

A prosthetic screen tacking device includes a barbed filament with a perpendicular foot at one end and a loop at the other. The barbs are situated near the foot and angulated in such a manner that they permit movement of the device through tissue in one direction (toward the loop), but prevent movement in the opposite direction (toward the foot). Different barbs and feet are shown. Methods of using the device with or without an associated button are also disclosed.

27 Claims, 5 Drawing Sheets

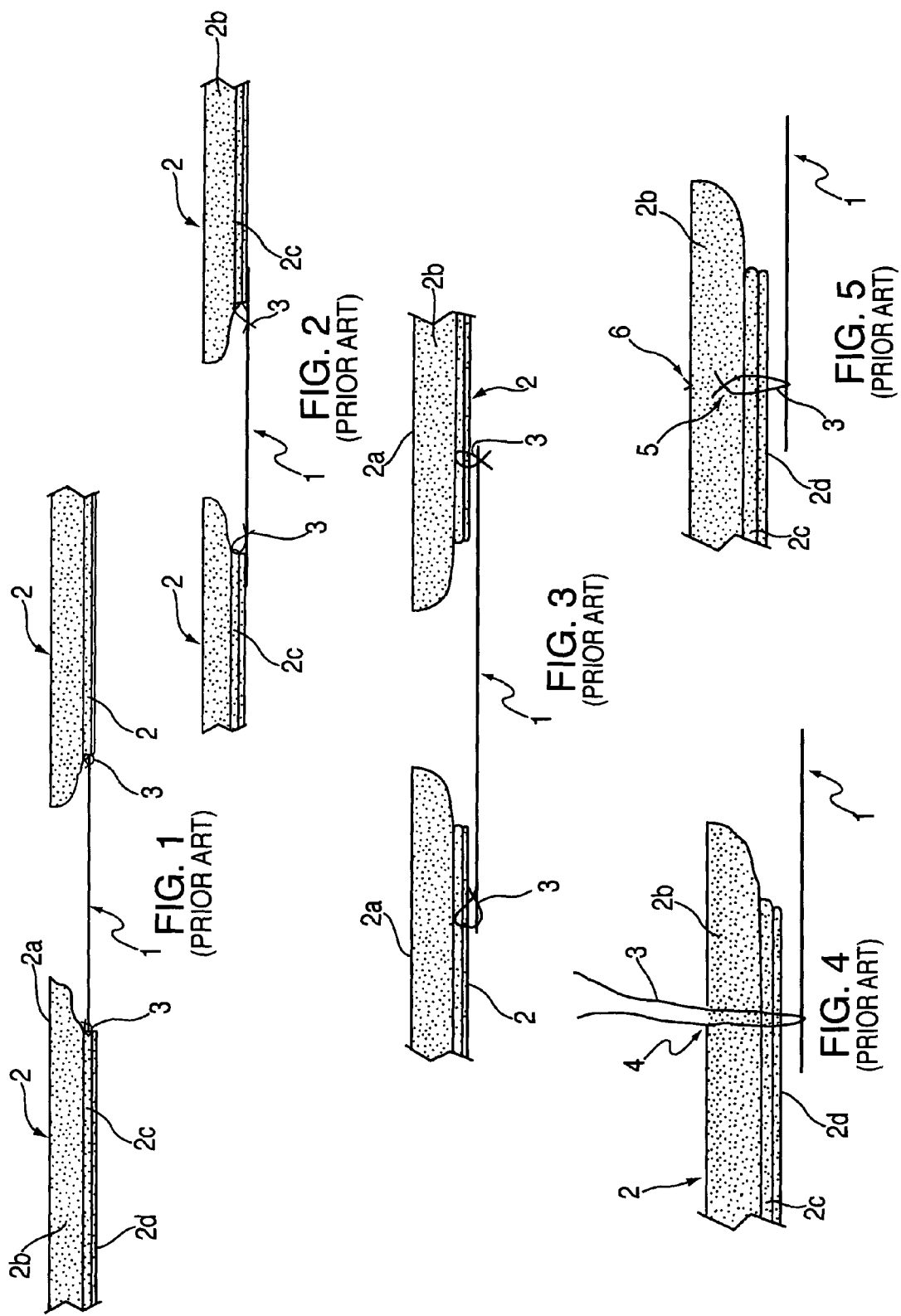

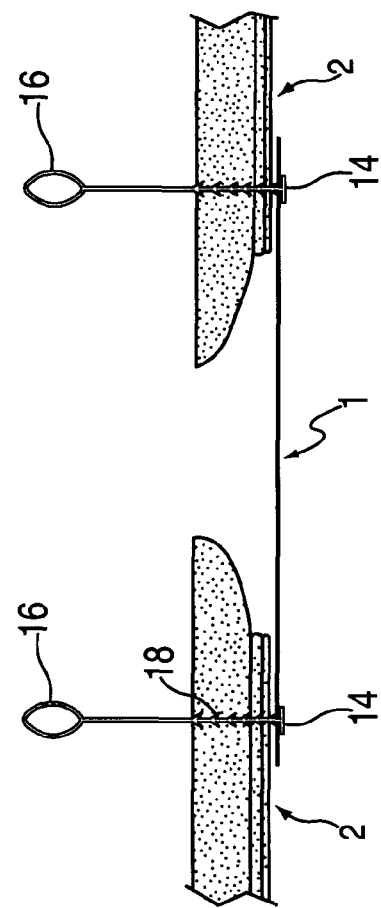
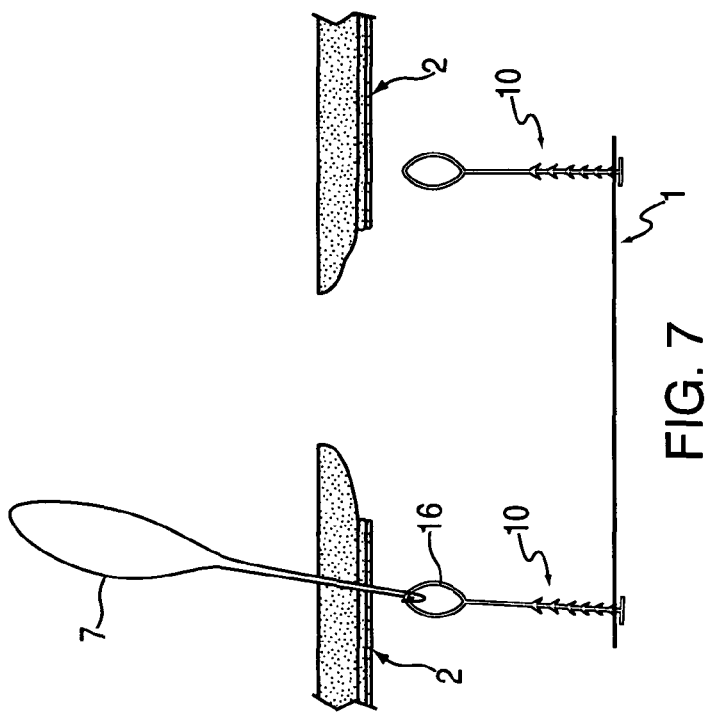
FIG. 7
FIG. 8

DEVICE AND METHOD FOR TACKING A PROSTHETIC SCREEN

BACKGROUND OF THE INVENTION

1. Field of the Invention

The invention relates to a device and method which simplifies the attachment of a prosthetic screen to the abdominal wall during the repair of abdominal wall hernias.

2. Brief Description of the Prior Art

The layer or layers of fascia which lie in the abdominal wall and surround the peritoneal cavity are the strong structures which maintain the integrity of the peritoneal cavity. If there is a defect in the fascia, abdominal contents may penetrate weaker layers of the abdominal wall (comprised of muscle or fat) and push ahead the abdominal cavity's thin lining (peritoneum) so that abdominal contents, such as omentum or bowel, within their envelope of peritoneum, become situated in a subcutaneous position, often causing a visible bulge.

Viscera being squeezed through a fascia defect can cause pain. When a visceral structure becomes trapped outside the fascial plane, it is said to be incarcerated. Incarcerated viscera can be strangulated by a narrow fascial defect, producing ischemic necrosis. This may lead to infection and death if not surgically repaired. Hernias are therefore usually repaired electively, before they become incarcerated or strangulated.

Historically, hernias of the abdominal wall were repaired by closing the fascial defect with sutures. Large hernias tend to recur if closed in this way. Prosthetic screens, made of plastic mesh or sheets, are now frequently used to cover large fascial defects. One way to implant the prosthetic screen is illustrated in prior art FIG. 1. Here, the prosthesis 1 is attached to the fascia 2c of the abdominal wall 2 with sutures 3. This is relatively easy to do, but the repair has a high rate of failure because the sutured prosthesis often pulls away from the fascial edge.

Other ways to secure prosthetic screens are shown in prior art FIGS. 2–5. In each of these methods the prosthesis 1 overlaps the edge of the fascia 2c. These methods are less likely to fail. Increased intra-abdominal pressure tends to force the periphery of the prosthesis against the abdominal wall rather than pull the prosthesis away from the fascia. A gap where both prosthesis and fascia are absent is less likely to develop.

If the prosthetic screen is allowed to overlap the edges of the fascial defect, there are a number of ways it can be secured in place as illustrated in prior art FIGS. 2–5. The sutures 3 can secure the fascia 2c to the prosthesis 1 inward from the edge of the prosthesis as shown in prior art FIG. 2. This is technically easy when the surgery is done in the conventional approach. However materials such as Gortex™ or polypropylene mesh used for prosthetic screens are soft and may buckle and deform outside the suture line, so that the structural advantage of the overlap with fascia is not realized.

A better method is to secure the prosthesis 1 to the abdominal wall fascia 2c with sutures 3 as close to the edge of the prosthesis as possible, while maintaining generous overlap between prosthesis and intact fascia as shown in prior art FIG. 3. However, it can be difficult to secure an overlapping intraperitoneal prosthesis at its periphery when performing surgery using a conventional approach. Access to the inside surface of the abdominal wall overlying the periphery of the prosthesis is limited. The more the overlap, the more difficult the access.

In order to achieve generous overlap the surgeon may bring the sutures through the abdominal wall as shown in prior art FIGS. 4 and 5. The midpoint of a suture 3 may be tied to the edge of the prosthesis 1, and the two ends brought out directly through the abdominal wall 2 near one another, through a single small separate incision 4 in the skin 2a as shown in prior art FIG. 4. Both ends of this transmural suture 3 are then tied together, placing the knot 5 beneath the skin in the subcutaneous tissue 2b as shown in prior art FIG. 5. The skin incision 4 is closed separately with skin sutures 6 or staples (not shown). This process is completed around the periphery of the prosthesis.

If surgery is done by a minimally invasive technique (e.g. laparoscopic surgery), the surgeon's view is from within the abdominal cavity looking up at the anterior abdominal wall. The periphery of the prosthesis can be fixed to the abdominal wall by direct suture (using a laparoscopic suture technique), or by using one of several fixation devices, such as staples or helical tacks. Alternatively, sutures can be fixed to the prosthesis before it is introduced into the peritoneal cavity. Once the prosthesis is correctly positioned, both ends of these sutures can be pulled through the abdominal wall and the same small skin incision and the ends tied together, placing the knot subcutaneously. Transmural sutures provide the most secure fixation of prosthetic screens. Hernia recurrence rates are lower when transmural sutures are used. A combination of techniques, using a few transmural sutures, at equidistant points along the periphery of the prosthesis, with staples or helical tacks in between, is also useful.

Despite the many advances made in laparoscopic suturing techniques as well as in open hernia repair, there are still many problems to be overcome. One problem is that in order to secure the prosthesis to the abdominal wall at a single point with a transmural suture, each suture end must be pulled separately through the abdominal wall. This is time consuming. Another problem is that after placement of both ends of each suture through the abdominal wall, they must be clamped together above the body wall while other transmural sutures are placed, because it is much easier to place transmural sutures before the prosthesis is hoisted up against the abdominal wall. Clamping insures that suture ends do not inadvertently pull out of the abdominal wall during this process. A large number of clamps clutter the operative field and the sutures and clamps tend to entangle one another. Furthermore, multiple short skin incisions must be made to set the knot of each tied pair subcutaneously. This process is somewhat time consuming and the multiple skin incisions produce a poor cosmetic result. Moreover, when two strands of suture are tied subcutaneously to secure a prosthetic screen, tissues of the abdominal wall are captured and partially strangulated within the ligature. This often produces postoperative pain and cosmetically undesirable dimpling of the skin at the ligature sites.

SUMMARY OF THE INVENTION

It is therefore an object of the invention to provide a device and method to fix a prosthetic screen to the abdominal wall.

It is another object of the invention to provide a device and method to fix a prosthetic screen to the abdominal wall which is applicable to both the open and laparoscopic methods of hernia repair.

It is still another object of the invention to provide a device and method to fix a prosthetic screen to the abdominal wall which requires penetrating the abdominal wall only once for each point of fixation.

It is yet another object of the invention to provide a device which is more easily grasped by a suture passer than is a single strand of suture.

It is a further object of the invention to provide a device which impedes accidental withdrawal once it is passed through the abdominal wall.

It is also an object of the invention to provide a device and method to fix a prosthetic screen to the abdominal wall which does not require the tying of sutures.

It is another object of the invention to provide a device and method to fix a prosthetic screen to the abdominal wall which does not require a skin incision to obtain subcutaneous fixation.

It is still another object of the invention to provide a device and method to fix a prosthetic screen to the abdominal wall which does not strangulate tissues of the abdominal wall.

In accord with these objects which will be discussed in detail below, the prosthetic screen tacking device according to the invention includes a barbed filament with a perpendicular foot at one end and a loop at the other. The foot may be a linear form, so that end of the device forms a T. The barbs are situated near the foot and angulated in such a manner that they permit movement of the device through tissue in one direction (toward the loop), but prevent movement in the opposite direction (toward the foot).

Using the open method of hernia repair, several tacking devices are pulled through the prosthetic screen equidistantly along the periphery (circumference) of the prosthesis. The assembly is then positioned within the open abdominal cavity, over the viscera. A suture passer (a needle-like implement with the ability to grasp sutures, e.g. a Reverdin needle) is then used to penetrate the abdominal wall at a point opposing the location where one tacking device penetrates the prosthesis, a point substantially beyond the edge of the fascial defect. The suture passer grasps the loop of the tacking device, and draws it back through the abdominal wall, so that the loop lies external to the body. The loop is then disengaged from the suture passer. The tacking device remains in place because the loop impedes accidental withdrawal from the abdominal wall. The same action is repeated until the loops of all devices are passed through the abdominal wall. Each device is then pulled further through the abdominal wall by grabbing the loop and pulling upward. The devices are pulled as far as possible using appropriate force to draw the prosthesis against the abdominal wall. This action draws the barbs into the abdominal wall and through at least one fascial layer. Each device is then pulled by its loop under tension. The skin, where penetrated by the device, is simultaneously pressed downward, further compressing the abdominal wall, and the filament is severed at skin level. Pressure is released, the abdominal wall expands and the severed end of the filament recedes beneath the skin. The barbs on the remaining portion of the filament prevent dislodgement of the device which prevents the prosthesis from pulling away from the abdominal wall. The abdominal wound above the prosthesis is closed as completely as possible by standard technique, and the operation is concluded.

The tacking device of the invention can be similarly utilized in a laparoscopic procedure. Here the devices are loaded onto the periphery of the prosthesis, the assembly is rolled up or folded introduced through a cannula or port site into the peritoneal cavity. Within the peritoneal cavity the assembly is unrolled or unfolded and oriented so that the loops are upward towards the abdominal wall. A suture passer is then used to penetrate the abdominal wall at a point corresponding to the preferred point of fixation of a particular device and the procedure proceeds substantially the same as described above.

One advantage of the tacking device of the invention over the conventional transmural suture is that it requires one filament rather than two suture ends to be drawn through the abdominal wall to secure the prosthesis at any point on its periphery. Thus, half the work is required.

Another advantage is that the loop of the device provides an excellent handle which a suture passer can grasp more easily than a single suture strand.

Another advantage is that once pulled through the abdominal wall the device will not be inadvertently withdrawn, since the loop will prevent withdrawal. Conventional sutures on the other hand can be accidentally withdrawn if not secured by a surgical clamp.

Another advantage is that no knot is required.

Another advantage is that no skin incision is required to place a knot subcutaneously.

Another advantage is that, unlike a transmural suture, this tacking device will not strangulate tissue of the abdominal wall and therefore will not produce as much postoperative pain.

Another advantage is that, unlike a transmural suture, this device will not produce cosmetically undesirable dimpling of the skin.

Furthermore, a knot below a skin incision is more likely to become infected than is the single filament of the tacking device of the invention, which retracts into the abdominal wall well below a small skin puncture site. Infectious agents are then less likely to travel down to infect the prosthetic screen. Use of the tacking device of the invention will result in fewer prosthetic screen infections, which are a major cause of morbidity, re-operation and recurrent hernia. Infected prosthetic screens must often be removed to control infection.

BRIEF DESCRIPTION OF THE DRAWINGS

FIGS. 1–5 illustrate prior art methods of securing a prosthetic screen;

FIGS. 7–10 illustrate how the novel prosthetic screen tacking device is used in conventional open surgery;

DETAILED DESCRIPTION

Figure 6:
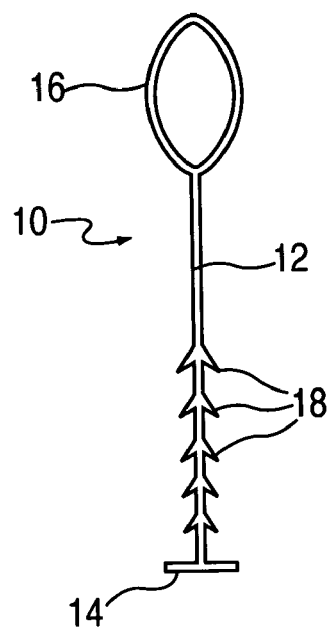
FIG. 6 is a side elevational view of a prosthetic screen tacking device according to the invention.

Turning now to FIG. 6, a prosthetic screen tacking device 10 includes a filament 12 with a perpendicular foot 14 at one end and a loop 16 at the other end. A plurality of barbs 18 are provided adjacent to the foot 14. The foot 14 may be a linear form, so that end of the device forms a T or may have other configurations as described in more detail below with reference to FIGS. 13–15. The barbs 18 are angulated in such a manner that they permit movement of the device through tissue in one direction (toward the loop 16), but prevent movement in the opposite direction (toward the foot 14).

FIGS. 7–10 illustrate how the tacking device 10 is used in the open method of hernia repair. Several devices 10 are pulled through the prosthetic screen 1 equidistantly along the periphery (circumference) of the prosthesis 1. The assembly is then positioned within the open peritoneal cavity, over the viscera (FIG. 7). A suture passer 7 (e.g. a Reverdin needle) is then used to penetrate the abdominal wall at a point opposing the location where one device penetrates the prosthesis, a point substantially beyond the edge of the fascial defect. The suture passer 7 grasps the loop 16 of the device and draws it back through all layers of the abdominal wall 2, including the peritoneum 2d, fascia 2c, muscle if present (not shown), subcutaneous tissue 2b and skin 2a, so that the loop lies external to the body. The loop is then disengaged from the suture passer. The tacking device will remain in place, because substantial force is necessary to withdraw the loop even before the barbs engage the abdominal wall. The same action is repeated until the loops of all devices are pulled through the abdominal wall.

Each device 10 is then pulled further through the abdominal wall by grabbing the loop and pulling upward so that the barbs 18 engage the abdominal wall as shown in FIG. 8. The devices are pulled as far as possible using appropriate force to draw the prosthesis 1 against the abdominal wall 2. When all devices have been pulled in this fashion the prosthesis is secured against the abdominal wall circumferentially.

Figure 9:
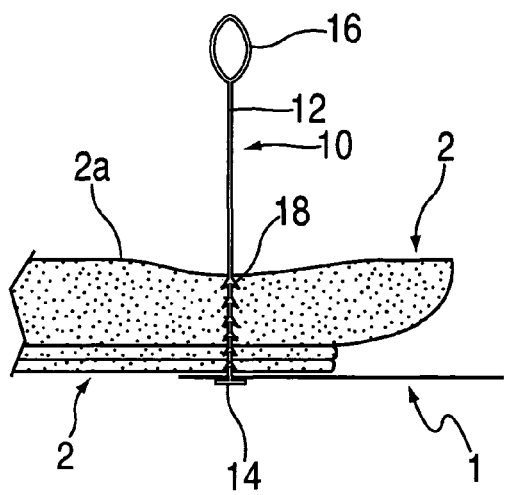
Figure 10:
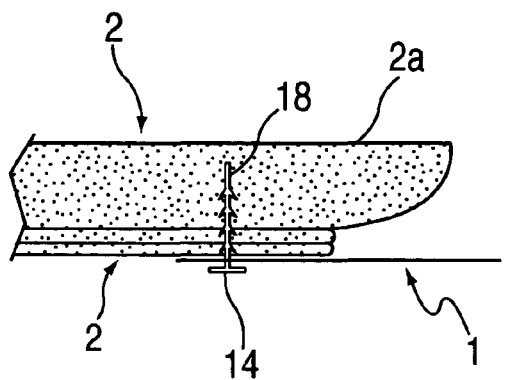

Each device 10 is then pulled by its loop 16 under tension. The skin 2a, where penetrated by the device, is simultaneously pressed downward as shown in FIG. 9, further compressing the abdominal wall, and the filament is severed at skin level. Pressure is released, the abdominal wall re-expands and the severed end of the filament recedes beneath the skin as shown in FIG. 10. The barbs 18 on the remaining portion of the filament prevent dislodgement of the device, which prevents the prosthesis 1 from pulling away from the abdominal wall 2. The abdominal wound above the prosthesis 1 is closed as completely as possible by standard technique, and the operation is concluded.

Figure 11:
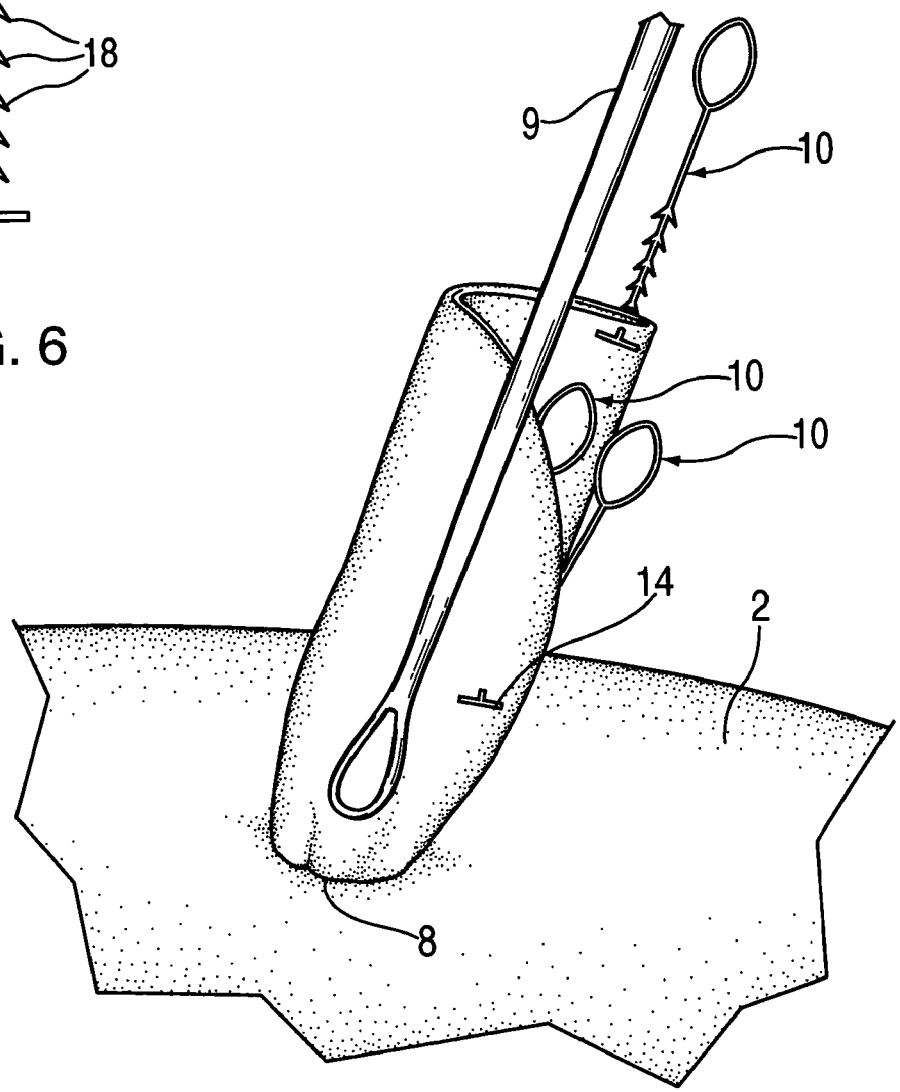
FIGS. 11–12 illustrate how the prosthetic screen tacking device is used in laparoscopic surgery.
Figure 12:
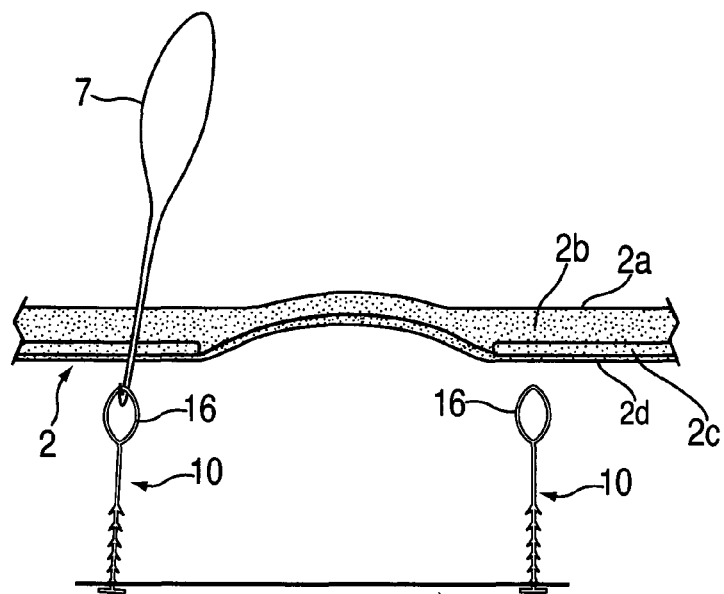

The tacking device 10 can be similarly utilized in a laparoscopic procedure. Here the devices are loaded onto the periphery of the prosthesis. The assembly of prosthesis and tacking devices is rolled up or folded and introduced into the peritoneal cavity through a cannula or, with the aid of a tool 9, through a port site 8 in the abdominal wall 2 (FIG. 11). The assembly is unrolled or unfolded and oriented within the peritoneal cavity so that the loops 16 are upward towards the abdominal wall (FIG. 12). The procedure continues in substantially the same manner as described above with reference to FIGS. 8–10.

The devices 10 may be color coded so that they may be more easily identified for handling in the proper sequence. They may be made of a biodegradable and absorbable material (e.g., polydioxanone, polyglycolide, etc.) so that they disintegrate and disappear after the prosthetic screen is naturally integrated into the abdominal wall and no longer able to dislodge.

Figure 13:
FIGS. 13–15 illustrate different embodiments of the foot of the tacking device.
Figure 14:
Figure 15:

As mentioned above, the geometry of the foot can vary. Three examples are shown in FIGS. 13–15. FIG. 13 shows a linear foot 14a. FIG. 14 shows a circular foot 14b, and FIG. 15 shows an elliptical foot 14c.

Figure 16:
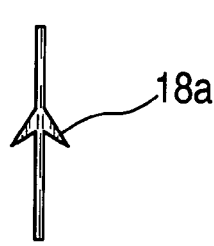
FIGS. 16–18 illustrate different embodiments of the barbs of the tacking device.
Figure 17:
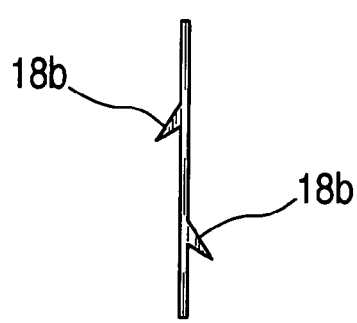
Figure 18:
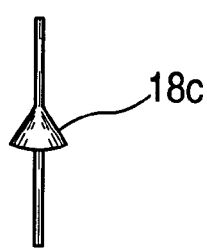

As mentioned above, the configuration of the barbs 18 may also vary. FIG. 16 shows bilateral barbs 18a. FIG. 17 shows unilateral barbs 18b which may alternate on different sides of the filament, or be positioned along different planes with respect to the axis of the filament. FIG. 18 shows conical barbs 18c.

Figure 19:
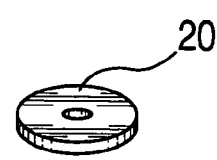
FIGS. 19–23 illustrate embodiments of a button that can be passed over the filament in order to further secure the tacking device and prevent its withdrawal from the abdominal wall.
Figure 20:
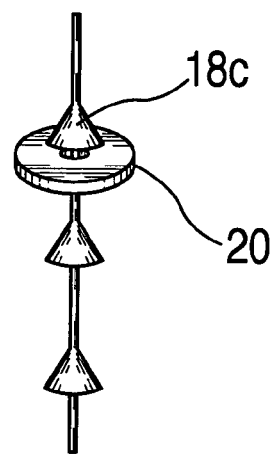

The tacking device of the invention may also be used in conjunction with a button 20 as shown in FIGS. 19 and 20. After the loop is pulled through the body tissue, the loop is pulled through the button 20 and the button is advanced downward along the filament until it locks behind barbs, e.g. 18c as shown in FIG. 20. It will be appreciated that the button 20 may be used with any of the barbs described above. The button 20 preferably has an outer diameter which is substantially larger than the width of the barbs. This makes it even more difficult for the tacking device to be withdrawn in the direction of the foot, securing the prosthesis even more. The button may be allowed to sit on the surface of the skin, or be buried subcutaneously through a small skin incision. The button shown in FIGS. 19 and 20 is a simple perforated disk, sufficiently plastic so that the barb 18c can be passed through the disk in one direction, but not the other.

Figure 21:
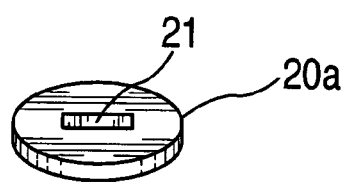
Figure 22:
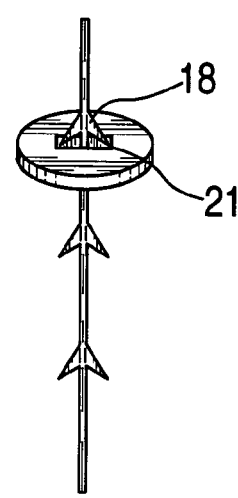
Figure 23:
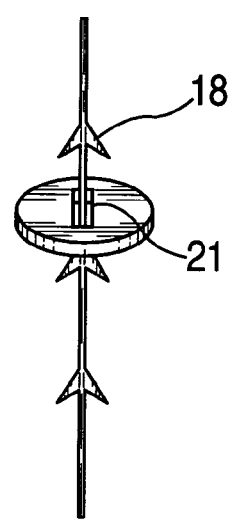

A different kind of button 20a is shown in FIGS. 21–23. The button 20a is provided with a slot 21. The slot allows it to pass over the barbs 18 when rotated to a first orientation shown in FIG. 22. When the button is rotated to a second orientation, shown in FIG. 23, it cannot be withdrawn.

There have been described and illustrated herein a device and method for affixing a prosthesis to the abdominal wall. While particular embodiments of the invention have been described, it is not intended that the invention be limited thereto, as it is intended that the invention be as broad in scope as the art will allow and that the specification be read likewise. It will therefore be appreciated by those skilled in the art that yet other modifications could be made to the provided invention without deviating from its spirit and scope as so claimed.

The invention claimed is:

1. A surgical tacking device suitable for the fixation of a prosthetic screen, said device comprising:
   a filament having a first end and a second end;
   a plurality of barbs arranged on said filament between said first and second ends, said barbs being configured and angulated to allow said filament to pass through body tissue when said first end is pulled but to prevent said filament from passing through body tissue when said second end is pulled; and
   a loop on said first end of said filament.

2. The surgical tacking device according to claim 1, wherein said barbs are arranged in side by side pairs.

3. The surgical tacking device according to claim 1, wherein said barbs are arranged in an alternating configuration.

4. The surgical tacking device according to claim 1, wherein said barbs are arranged in a random configuration.

5. The surgical tacking device according to claim 1, wherein said barbs are conical structures.

6. The surgical tacking device according to claim 1, further comprising a button arranged to slide over said barbs when moved over said filament from said first end toward said second end but unable to slide over said barbs when moved from said second end toward said first end.

7. The surgical tacking device according to claim 1, further comprising a button configured to slide over said barbs when rotated to a first position but unable to slide over said barbs when rotated to a second position.

8. The surgical tacking device according to claim 1, wherein said device is made of a biodegradable material.

9. The surgical tacking device according to claim 1, wherein said filament, barbs and loop are formed in one piece.

10. The surgical tacking device according to claim 1, further comprising: a foot on said second end of said filament, said foot arranged to prevent said second end of said filament from passing through a prosthetic screen.

11. The surgical tacking device according to claim 10, wherein said foot is substantially linear in shape.

12. The surgical tacking device according to claim 10, wherein said foot is substantially circular.

13. The surgical tacking device according to claim 10, wherein said foot is substantially elliptical.

14. The surgical tacking device according to claim 10, further comprising a button arranged to slide over said barbs when moved over said filament from said first end toward said second end but unable to slide over said barbs when moved from said second end toward said first end.

15. The surgical tacking device according to claim 10, further comprising a button configured to slide over said barbs when rotated to a first position but unable to slide over said barbs when rotated to a second position.

16. The surgical tacking device according to claim 10, wherein said device is made of a biodegradable material.

17. The surgical tacking device according to claim 10, wherein said filament, barbs, loop and foot are formed in one piece.

18. A method for affixing a prosthetic screen to the wall of the abdomen, said method comprising:
   attaching a plurality of surgical tacking devices to the screen, the tacking devices including a filament having a first end and a second end with a loop at said first end and a plurality of barbs between said first and second ends;
   delivering the screen with attached tacking devices to the peritoneal cavity; and
   pulling the loop of each tacking device through the abdominal wall so that the barbs of the device lodge in the abdominal wall and affix the prosthesis to the abdominal wall.

19. The method according to claim 18, further comprising cutting said tacking devices at a point between said first and second ends.

20. The method according to claim 18, wherein said step of delivering includes delivering the screen and attached tacking devices into the peritoneal cavity through a port site.

21. A method for affixing a prosthetic screen to the wall of the abdomen, said method comprising:
   attaching a plurality of surgical tacking devices to the screen, the tacking devices including a filament having a first end and a second end with a loop at said first end, a foot at said second end, and a plurality of barbs between said first and second ends;
   delivering the screen with attached tacking devices to the peritoneal cavity; and
   pulling the loop of each tacking device through the abdominal wall.

22. The method according to claim 21, further comprising:
   cutting said tacking devices at a point between said first and second ends.

23. The method according to claim 21, wherein:
   said step of delivering includes delivering the screen and attached tacking devices into the peritoneal cavity through a port site.

24. A method for affixing a prosthetic screen to the wall of the abdomen, said method comprising:
   attaching a plurality of surgical tacking devices to the screen, the tacking devices including a filament having a first end and a second end with a foot at said second end and a plurality of barbs between said first and second ends;
   delivering the screen and attached tacking devices to the peritoneal cavity of the abdomen; and
   pulling the filament of each tacking device through the abdominal wall so that the barbs of the device lodge in the abdominal wall and affix the prosthesis to the abdominal wall.

25. The method according to claim 24, further comprising cutting said tacking devices at a point between said first and second ends so that when the surgical procedure is concluded in parts of the tacking devices penetrate into or through the skin.

26. The method according to claim 24, wherein said step of delivering includes delivering the screen and attached tacking devices into the peritoneal cavity through a port site when performing laparoscopic hernia repair.

27. The method according to claim 24, wherein said step of delivering includes delivering the screen and attached tacking devices into the peritoneal cavity when performing open hernia repair.

* * * * *